United States Patent [19]

Freud

[11] 4,429,343
[45] Jan. 31, 1984

[54] HUMIDITY SENSING ELEMENT

[75] Inventor: Paul J. Freud, Furlong, Pa.

[73] Assignee: Leeds & Northrup Company, North Wales, Pa.

[21] Appl. No.: 326,794

[22] Filed: Dec. 3, 1981

[51] Int. Cl.$^3$ ............................................. H01G 5/20
[52] U.S. Cl. ..................................... 361/286; 73/336.5
[58] Field of Search ........................ 361/283, 303, 304; 73/29, 336.5, 303, 304, 286, 283

[56] References Cited

U.S. PATENT DOCUMENTS

| | | | |
|---|---|---|---|
| 2,707,880 | 5/1955 | Wannamaker | 73/336.5 |
| 2,828,454 | 3/1958 | Khouri | 361/304 |
| 3,802,268 | 4/1974 | Thoma | 73/336.5 |

FOREIGN PATENT DOCUMENTS 707930  8/1955  Australia .............................. 361/303

OTHER PUBLICATIONS

Channon "A Thick Film Humidity Sensor" Conf. on Hybrid Microelectronics, Loughborough, Leics England 9-11 Sept. 1975 pp. 57-62.
Birks "Modern Dielectric Materials" Haywood & Co. London 1960 pp. 150-154.

*Primary Examiner*—Donald A. Griffin
*Attorney, Agent, or Firm*—William G. Miller, Jr.; Harold Huberfeld

[57] ABSTRACT

A humidity sensing element of the capacitance sensing type having two sets of interdigitated fingers of thin film platinum deposited on a glass substrate, all covered by a coating of water absorbing material such as cellulose acetate butyrate or a silicone rubber. The coating is of thickness such that it is substantially equal to or greater than the period of the fingers of the interdigitated electrodes.

4 Claims, 3 Drawing Figures

HUMIDITY SENSING ELEMENT

BACKGROUND OF THE INVENTION

This invention relates to an improved capacitance humidity sensing element for use in humidity measuring and control systems.

Humidity can be measured by a number of techniques which are based upon the reversible water absorption characteristics of polymeric materials. The absorption of water causes a number of physical changes in the polymer. These physical changes can be transduced into electrical signals which are related to the water concentration in the polymer and which in turn are related to the relative humidity in the air surrounding the polymer. Two of the most common physical changes are the change in resistivity and the change in dielectric constant which can be respectively translated into a resistance change and a capacitance change. Arrangements utilizing the resistance change may, for example, be constructed in accordance with U.S. Pat. No. 3,559,456 issued on Feb. 2, 1971, to F. Lomker et al. It has been found, however, that elements utilized as resistive components suffer from the disadvantage that there is an inherent dissipation effect caused by the dissipation of heat due to the current flow in the elements necessary to make a resistance measurement. The result is erroneous readings.

Elements constructed to approximate a pure capacitance avoid the disadvantages of the resistive elements. However, it is important in the construction of capacitive elements to avoid the problems which can arise with certain constructions for such elements. Exemplary of the capacitive type element is that shown in U.S. Pat. No. 3,802,268 issued to Paul E. Thoma on Apr. 9, 1974. In that patent a sheet of cellulose acetate butyrate is sandwiched between two planar electrodes, one of which is porous to allow water molecules to equilibrate with the bulk of the film. Among the problems which are encountered with this type of construction is the slow response due to the thickness required to support the structure. There is also a difficulty in fabricating a conductive yet porous electrode. In addition, there is also inaccuracy incurred at high relative humidity values in that the high water content causes problems due to excessive stress and the resulting mechanical shifts in the components of the element.

By making the component parts of the element thin, the above mentioned problems can be avoided and the capacitance type element can provide a fast, precise measurement of the relative humidity content of air over an extreme range of humidity as well as over an extreme range of temperature and pressure and other environmental variables.

Humidity sensing elements of the capacitance sensing type usually include a moisture insensitive, non-conducting structure with appropriate electrode elements mounted or deposited on the structure along with a layer or coating of dielectric, highly moisture sensitive material overlaying the electrodes and positioned so as to be capable of absorbing water from the surrounding atmosphere and reaching equilibrium in a short period of time.

This invention discloses a capacitive sensing element in which all of the difficulties of the above mentioned element of U.S. Pat. No. 3,802,268 are avoided. This improved structure utilizes a planar interdigitated electrode structure to form the capacitor. The electrode structure is advantageously made of thin film metal deposited on a suitable non-conducting substrate and patterned to form two sets of interdigitated fingers. Each set of the interdigitated fingers is connected in parallel to a separate bus and a contact. The capacitance between the two sets of fingers is, of course, determined by the spacing between the fingers, the width and length of the fingers, the number of fingers, and the dielectric constant of the material applied over the fingers to coat the surface of the element. The humidity sensitivity of course arises from the humidity-related dielectric constant changes which occur in the coating over the fingers, for all other parameters remain constant. In the present invention, a polymer such as cellulose acetate butyrate is utilized to provide the humidity-related dielectric. This polymer coating must, of course, be made as thin as possible in order to have a short response time to changes in the relative humidity of the surrounding atmosphere. It has been found that one of the difficulties which arises with such a structure is the contamination of the outer surface of the polymer which can lead to a condensation on the surface at high humidities and which therefore leads to very non-linear and non-repeatable outputs from the elements. It is therefore an object of this invention to avoid such difficulties with contamination while maintaining a minimum response time for the elements.

SUMMARY OF THE INVENTION

In carrying out the present invention, there is provided a capacitance humidity sensing element which comprises a non-conducting substrate material which carries two separate interdigitated thin metal film electrodes deposited thereon, and which has a coating over these electrodes of a water absorbing polymer with the coating being of a thickness substantially equal to or greater than the period of the fingers of the interdigitated electrodes. With such a coating thickness, problems with contamination on the boundary can be avoided.

BRIEF DESCRIPTION OF THE DRAWINGS

In the Figures.

DESCRIPTION OF THE PREFERRED EMBODIMENT

Figure 1:
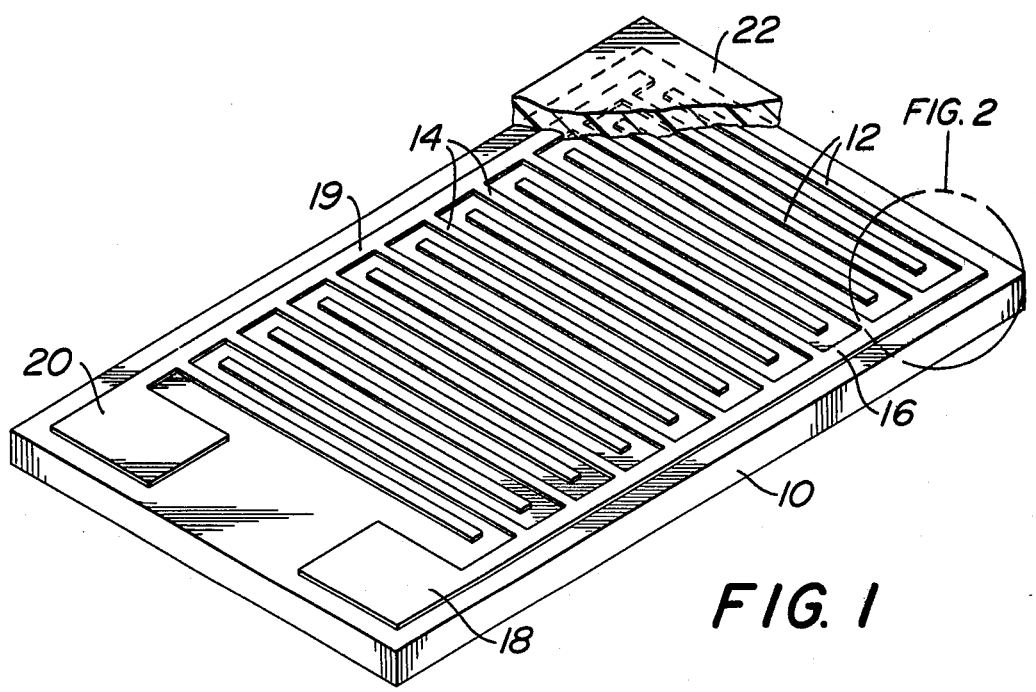
FIG. 1 is a perspective view of a humidity sensing element of the invention in one form wherein the electrodes are mounted on a thin planar substrate.

In FIG. 1 there is shown a planar non-conducting substrate 10 which may, for example, be constructed of borosilicate glass. On the surface of the substrate 10 there is deposited a thin metal film electrode system which is made up of a first set of fingers 12 which are located in an interdigitated configuration with a second set of fingers 14. The fingers 12 are all connected in parallel to a common bus 16 which is in turn connected to the contact structure 18 at which point electrical contact is made with the measuring instruments to be used.

Figure 2:
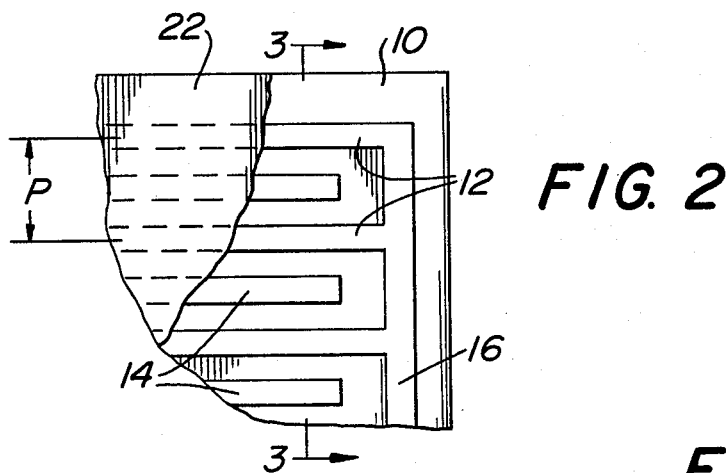
FIG. 2 is a plane view of an enlarged section of that element.

The other set of fingers 14 are connected in parallel to the bus 19 which is in turn connected to the contact 20, for which electrical connection is provided to the measuring instrument. The interdigitated fingers are more clearly shown in the enlarged portion of the element shown in FIG. 2 where it is shown that the distance from the center of a finger of one set to the center of the next finger of that set is identified as the period P.

Figure 3:
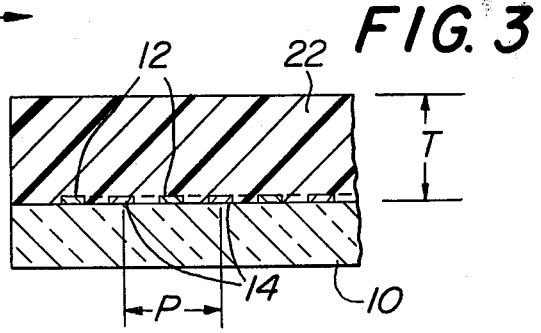
FIG. 3 is a cross-section of the element of FIG. 2 taken along the line A—A.

The structure of the element of FIG. 1 and its relationship to the polymer coating which overlays the fingers is shown in more detail in FIG. 3 where the polymer 22 is shown overlaying fingers 12 and 14 which are shown as being deposited on the non-conducting substrate 10. As shown in FIG. 3, the thickness of the polymer coating is, in accordance with this invention, greater than the period of the fingers so that there will be negligible effects resulting from the surface of the polymer coating such as might occur as the result of contamination. Since the capacitance between the sets of interdigitated fingers is determined by the weighted average of the dielectric constant of the polymer coating, that portion of the coating closest to the surface of the fingers must be weighted the most and that portion furthest from the fingers the least. Thus, it will be seen that if the coating is thick enough there will be portions of the coating, at its surface and away from the fingers, which will be a sufficient distance from the surface of the fingers so as to have a negligible effect on the average dielectric constant. Thus, if the coating is maintained thick enough to place the surface far enough from the finger surface, the influence of contaminants on the surface is negligible and an improved function can be obtained from the sensing element.

Devices of the type described above have been utilized to measure the relative humidity to an accuracy of 1% and a stability at 95% relative humidity of better than 1% in one month. The structure has been shown to be independent of surface conditions to better than 1% relative humidity when a coating 50 microns thick was placed over an interdigitated electrode structure having a period of 50 microns. The structure consisted of 12 micron wide fingers with 12 micron wide spaces between them resulting in a period of approximately 50 microns. The coating used was solvent cast cellulose acetate butyrate 50 microns thick. The capacitance of the 4mm×4 mm pattern was 30 picofarads with a 3 picofarad capacitance change in going from zero to 100% relative humidity.

It is also possible to use other water absorbing coatings such as silicone rubbers in place of the cellulose acetate butyrate.

What is claimed is:

1. A fast, precise capacitance humidity sensing element comprising:
   a planar non-conducting substrate;
   two separate closely spaced interdigitated thin metal film electrodes deposited on said substrate with fingers having a certain period; and a thin water absorbing coating covering said interdigitated electrodes, said coating being of thickness substantially equal to or greater than the period of the fingers of said interdigitated electrodes to place the surface of the coating far enough from the surface of the fingers so that the influence of contaminants on the coating surface is negligible.

2. A capacitance humidity sensing element as set forth in claim 1 in which said coating is a polymer.

3. A capacitance humidity sensing element as set forth in claim 2 in which said polymer is solvent cast cellulose acetate butyrate.

4. A capacitance humidity sensing element as set forth in claim 1 in which said coating is a silicone rubber.

* * * * *